United States Patent
Hudson

(10) Patent No.: US 10,227,971 B2
(45) Date of Patent: Mar. 12, 2019

(54) DOWNSTREAM FLOW DETECTION SYSTEM FOR FLOW CONTROL APPARATUS

(71) Applicant: KPR U.S., LLC, Mansfield, MA (US)

(72) Inventor: Joseph Hudson, O'Fallon, MO (US)

(73) Assignee: KPR U.S., LLC, Mansfield, MA (US)

( * ) Notice: Subject to any disclaimer, the term of this patent is extended or adjusted under 35 U.S.C. 154(b) by 407 days.

(21) Appl. No.: 14/818,387

(22) Filed: Aug. 5, 2015

(65) Prior Publication Data
US 2016/0045400 A1 Feb. 18, 2016

Related U.S. Application Data

(60) Provisional application No. 62/036,308, filed on Aug. 12, 2014.

(51) Int. Cl.
| | |
|---|---|
| *F04B 49/08* | (2006.01) |
| *F04B 49/02* | (2006.01) |
| *F04B 45/08* | (2006.01) |
| *F04B 43/12* | (2006.01) |
| *A61J 15/00* | (2006.01) |

(Continued)

(52) U.S. Cl.
CPC ........... *F04B 49/08* (2013.01); *A61J 15/0076* (2015.05); *A61M 5/16854* (2013.01); *A61M 5/16859* (2013.01); *A61M 5/365* (2013.01); *F04B 43/12* (2013.01); *F04B 45/08* (2013.01); *F04B 49/022* (2013.01); *A61M 5/14232* (2013.01);

(Continued)

(58) Field of Classification Search
CPC ................... F04B 49/08; F04B 49/022; F04B 43/12–43/14; F04B 45/08; A61J 15/0076; A61M 5/16859; A61M 5/16854; A61M 5/365; A61M 2206/10; A61M 5/14232; A61M 2205/3375; A61M 2005/16868; G05D 7/0676

See application file for complete search history.

(56) References Cited

U.S. PATENT DOCUMENTS

| | | |
|---|---|---|
| 4,271,844 A | 6/1981 | Croslin |
| 4,754,761 A | 7/1988 | Ramsey, III et al. |

(Continued)

FOREIGN PATENT DOCUMENTS

| | | |
|---|---|---|
| EP | 2777730 A1 | 9/2014 |
| WO | 2005119181 A1 | 12/2005 |

(Continued)

OTHER PUBLICATIONS

Written Opinion dated Feb. 24, 2016 in related International Application No. PCT/US2015/044132, 10 pages.

(Continued)

*Primary Examiner* — Bryan Lettman
(74) *Attorney, Agent, or Firm* — Adnan H. Bohri

(57) ABSTRACT

A flow control apparatus adapted to load a feeding set having an upstream side and a downstream side including a housing capable of receiving at least a portion of the feeding set. A pumping device contacts the feeding set when the feeding set is received by the housing so the pumping device acts on the feeding set to produce fluid flow in the feeding set for delivery of fluid to a subject. An ultrasonic sensor is arranged with respect to the pumping device to detect a change in pressure in the downstream side of the feeding set when the feeding set is loaded on the apparatus.

19 Claims, 14 Drawing Sheets

(51) Int. Cl.
*A61M 5/168* (2006.01)
*A61M 5/36* (2006.01)
*A61M 5/142* (2006.01)

(52) U.S. Cl.
CPC .............. *A61M 2005/16868* (2013.01); *A61M 2205/3375* (2013.01)

(56) References Cited

U.S. PATENT DOCUMENTS

| | | | |
|---|---|---|---|
| 4,946,070 A * | 8/1990 | Albert | A47K 5/1215 141/351 |
| 4,950,235 A | 8/1990 | Slate et al. | |
| 5,096,385 A | 3/1992 | Georgi et al. | |
| 5,328,460 A | 7/1994 | Lord et al. | |
| 5,989,222 A * | 11/1999 | Cole | A61M 5/16854 604/151 |
| 6,283,719 B1 | 9/2001 | Frantz et al. | |
| 7,092,797 B2 | 8/2006 | Gaines et al. | |
| 7,771,453 B2 | 8/2010 | McEwen et al. | |
| 7,875,004 B2 | 1/2011 | Yodfat et al. | |
| 8,287,488 B2 | 10/2012 | Wiegel | |
| 2005/0267439 A1 * | 12/2005 | Harr | A61M 5/14232 604/500 |
| 2006/0078448 A1 | 4/2006 | Holden | |
| 2006/0135907 A1 | 6/2006 | Remde et al. | |
| 2007/0083292 A1 * | 4/2007 | Knauper | A61M 5/14232 700/282 |
| 2010/0280434 A1 | 11/2010 | Raney et al. | |
| 2012/0065596 A1 * | 3/2012 | Haueter | A61M 5/14244 604/246 |
| 2013/0238261 A1 | 9/2013 | Denis et al. | |
| 2016/0022545 A1 * | 1/2016 | Boulanger | A61M 5/14232 604/67 |
| 2016/0022546 A1 * | 1/2016 | Hudson | A61J 15/0076 604/500 |

FOREIGN PATENT DOCUMENTS

| | | |
|---|---|---|
| WO | 2009124134 A2 | 10/2009 |
| WO | 2015048709 A1 | 4/2015 |

OTHER PUBLICATIONS

International Preliminary Report on Patentability dated Apr. 21, 2016 in related International Application No. PCT/US2015/044132, 11 pages.

International Search Report dated Nov. 13, 2015 in related International Application No. PCT/US2015/044132, 10 pages.

Written Opinion of the International Searching Authority dated Nov. 13, 2015 in related International Application No. PCT/US2015/044132, 8 pages.

* cited by examiner

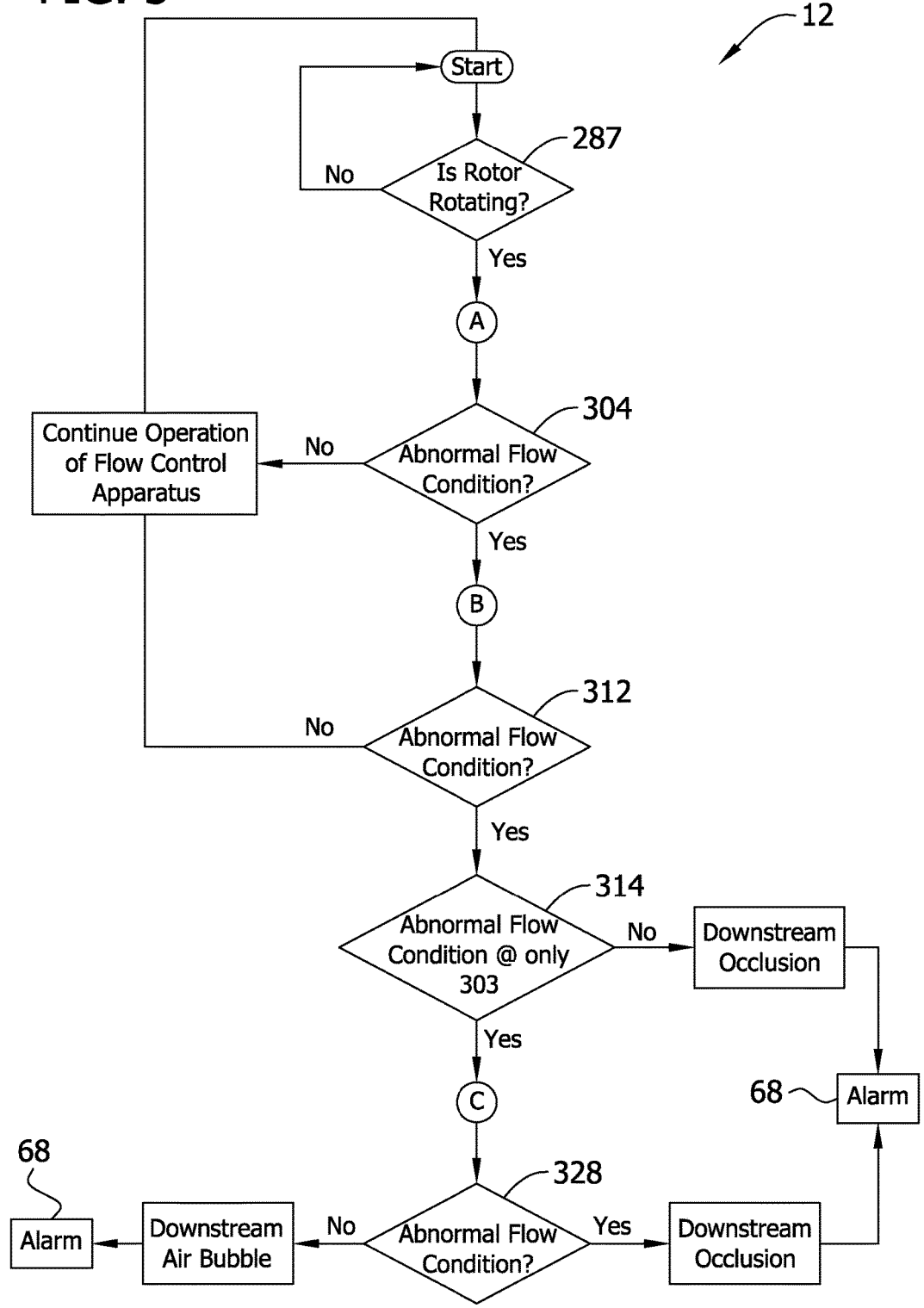

DOWNSTREAM FLOW DETECTION SYSTEM FOR FLOW CONTROL APPARATUS

CROSS-REFERENCE TO RELATED APPLICATION

The present application claims the benefit of U.S. Patent Application Ser. No. 62/036,308, entitled DOWNSTREAM FLOW DETECTION SYSTEM FOR FLOW CONTROL APPARATUS, filed Aug. 12, 2014, the complete disclosure of which is incorporated herein by reference for all purposes.

FIELD OF THE INVENTION

The present invention generally relates to a flow control apparatus capable of detecting a downstream flow condition in a tube set mounted on the apparatus.

BACKGROUND OF THE INVENTION

Administering fluids containing medicine or nutrition to a patient is known in the art. Typically, fluid is delivered to the patient by an administration feeding set loaded to a flow control apparatus, such as a pump, connected to a source of fluid which delivers fluid to a patient.

A flow control apparatus of the prior art may also be capable of monitoring and detecting fluid flow conditions that can occur within the loaded administration feeding set during operation of the flow control apparatus. Generally, prior art flow monitoring systems that are capable of monitoring and detecting flow conditions may rely on a sensor disposed at the upstream side of the administration feeding. However, sensors disposed at the upstream side of the feeding set can not directly and rapidly measure the condition of the feeding set at the downstream side where fluid is being delivered to the patient.

SUMMARY OF THE INVENTION

In a first aspect, a flow control apparatus adapted to load a feeding set having an upstream side and a downstream side generally comprises a housing capable of receiving at least a portion of the feeding set. A pumping device contacts the feeding set when the feeding set is received by the housing so the pumping device acts on the feeding set to produce fluid flow in the feeding set for delivery of fluid to a subject. An ultrasonic sensor is arranged with respect to the pumping device to detect a change in pressure in the downstream side of the feeding set when the feeding set is loaded on the apparatus.

The ultrasonic sensor can comprise a receiver assembly and an ultrasonic transmitter assembly, the transmitter assembly being configured to transmit an ultrasonic signal through the downstream side of the feeding set to the receiver assembly for determining the downstream flow condition of the feeding set when the feeding set is loaded on the apparatus.

A control circuit can be in communication with the ultrasonic sensor for receiving a sensor signal from the ultrasonic sensor indicative of the pressure in the downstream side of the feeding set, the control circuit being configured to determine the downstream flow condition of the feeding set while fluid is flowing through the feeding set.

The control circuit can include a memory, the control circuit being configured to save a series of sensor signal readings in the memory, the control circuit being configured to use the saved sensor signal readings to establish a baseline.

The control circuit can be configured to store a predetermined number of sensor signal readings in the memory including an oldest sensor signal reading and a newest sensor signal reading, and upon receiving a next sensor signal reading making the total number of sensor signal readings higher than said predetermined number, to discard the oldest sensor signal reading and store said next sensor signal reading as the newest sensor signal reading.

The control circuit can be configured upon receiving a new sensor signal reading to determine that the new sensor signal reading is above the baseline.

The control circuit can be configured upon receiving a new sensor signal reading when the pumping device is not operating to produce fluid flow to determine that the new sensor signal readings are falling below the baseline.

The control circuit can be configured to stop the pumping device at a predetermined position before receiving said new sensor signal readings or obtain new sensor signal readings while the pumping device is in operation.

The pumping device can comprise a motor and a rotor, the motor being adapted to rotate the rotor so that the rotor repeatedly contacts the feeding set to produce fluid flow through the feeding set. During this operation to monitor the ultrasonic signal for an increase in signal above the baseline due to the increase in pressure within the tube that would be due to a potential occlusion. The increase in ultrasonic signal above the baseline in response to the increase in pressure caused by the rotation of the rotor.

The pumping device is stopped at a predetermined position can that comprises of a rotational position of the rotor where fluid pressure in the feeding set is held (if occlusion is present), to monitor the ultrasonic signal for a continued increase in signal after rotor operation has stopped due to the continued presence of pressure within the tube.

The control circuit can be configured to cause further rotation of the rotor, the pressure in the feeding set releasing upon said further rotation when an occlusion is present, and to monitor the ultrasonic signal for a decrease in pressure below the high pressure condition generated during rotor operation.

This decrease in pressure allows the ultrasonic signal to decrease to a non-occluded level so that the next rotor operation can detect an increase in ultrasonic signal if an occlusion is present.

The pumping device can comprise a motor and a rotor, the motor being adapted to rotate the rotor so that the rotor repeatedly contacts the feeding set to produce fluid flow through the feeding set, the control circuit being configured to cease rotation of the rotor at a predetermined position causing pressure in the feeding set to decrease, and to monitor the ultrasonic signal for a decrease below the baseline.

The control circuit can be adapted to operate the pumping device in a verification routine after an initial determination that an occlusion may be present in the downstream portion of the feeding set for verifying the presence of the occlusion.

The pumping device can comprise a motor and a rotor, the motor being adapted to rotate the rotor so that the rotor repeatedly contacts the feeding set to produce fluid flow through the feeding set, and wherein the verification routine comprises causing the motor to turn the rotor through a partial rotation and monitoring sensor signal readings for an increase above a threshold.

In a second aspect, a method of operating a flow control apparatus can include a pumping device for detecting occlusions in fluid flow in a pump set acted upon by the flow control apparatus in a downstream portion of the pump set located downstream of the pumping device generally comprises receiving in a control circuit sensor signals from an ultrasonic sensor positioned to detect pressure in the downstream portion of the pump set. The received sensor signals are compared to a baseline stored in the control circuit, and the control circuit determines the presence of an occlusion in the downstream portion of the pump set using the comparison of the received sensor signals to the baseline.

The step of comparing can comprise determining if the received sensor signals are above the baseline when the pumping device is activated to pump fluid through the pump set.

The step of comparing can comprise determining if the received sensor signals are below the baseline when the pumping device is not operating to pump fluid through the pump set.

The determining step can include operating the pumping device for a partial cycle of the pumping device and monitoring the sensor signals for a rise in pressure above a predetermined amount.

The determining step can further include stopping a rotor of the pumping device in a predetermined position before monitoring the sensor signals for the rise in pressure above the predetermined amount.

The method can further comprise storing sensor signals readings from the ultrasonic sensor and using the stored sensor signals to establish the baseline.

Other aspects and features will be in part apparent and in part pointed out hereinafter.

BRIEF DESCRIPTION OF THE DRAWINGS

FIG. 5 is a flow chart of the flow monitoring system;

Corresponding reference characters indicate corresponding parts throughout the drawings.

DETAILED DESCRIPTION

Figure 1:
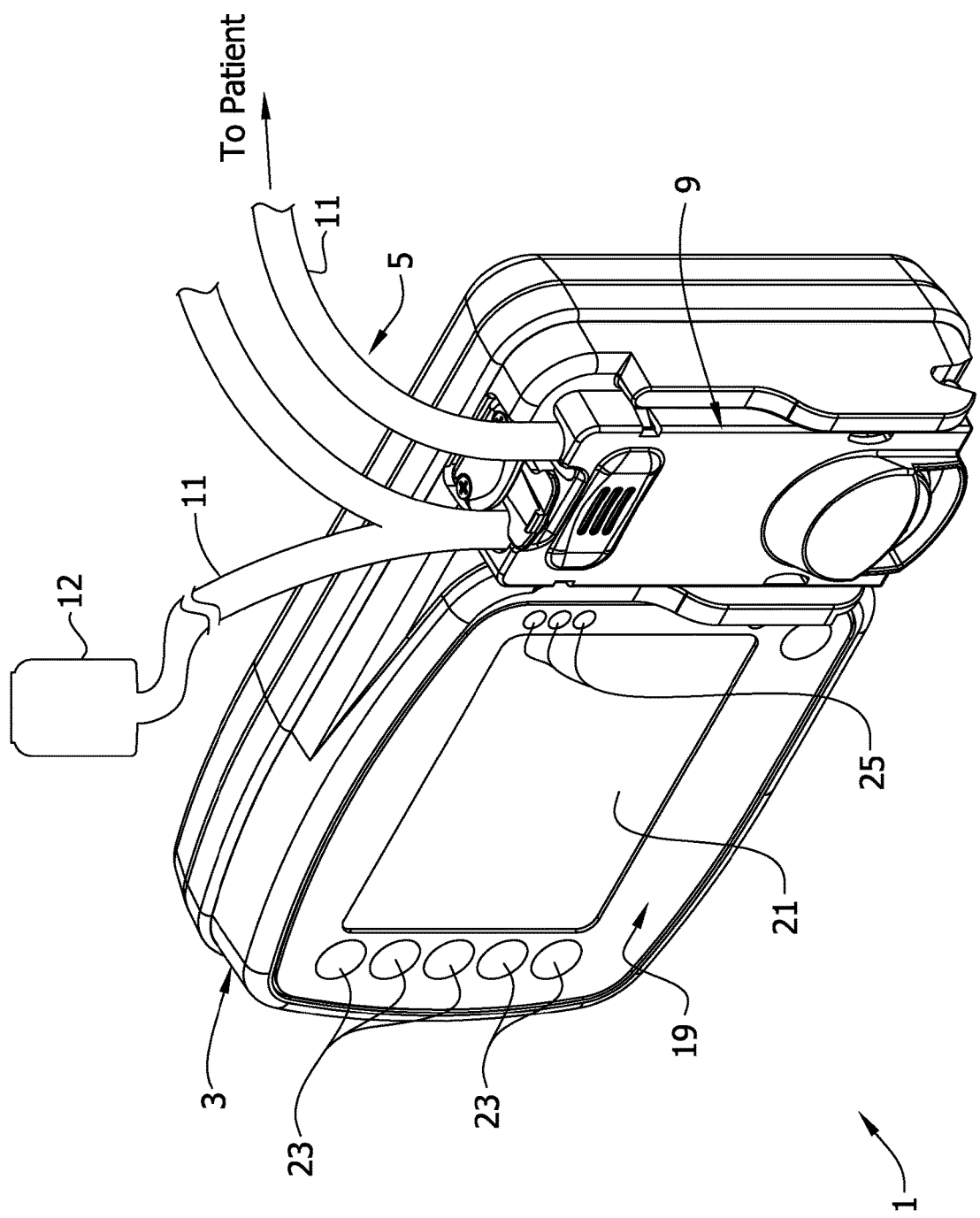
FIG. 1 is a perspective of an enteral feeding pump and a fragmentary portion of a feeding set (illustrated schematically) received on the pump.

Referring to the drawings and in particular to FIGS. 1-4, an embodiment of a flow control apparatus is generally indicated at 1. The flow control apparatus may comprise a flow monitoring system 4 (FIG. 4) that is capable of detecting and identifying a downstream flow condition present within a feeding set 5 loaded on the apparatus. The feeding set 5 may include tubing 11 that can be loaded on the flow control apparatus 1 for delivery of fluid to a patient by engaging a valve mechanism 28 and mounting member 13 of the feeding set to the flow control apparatus. As used herein, the term load means that the valve mechanism 28 and mounting member 13 are engaged to the flow control apparatus 1 such that the administration feeding set 5 is ready for operation with the flow control apparatus 1.

Figure 2:
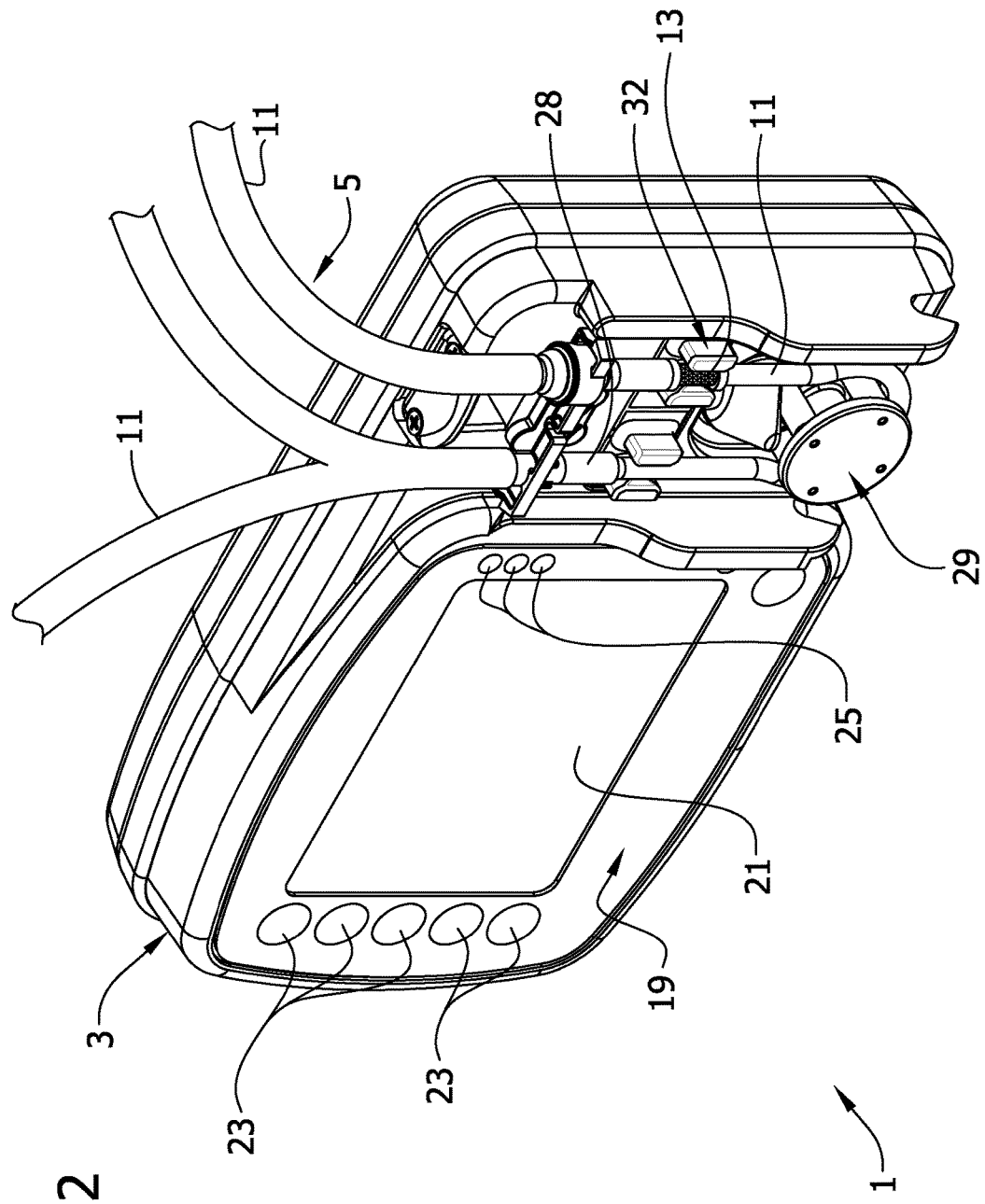
FIG. 2 is a perspective of FIG. 1 with a cassette housing of the feeding set removed.
Figure 3:
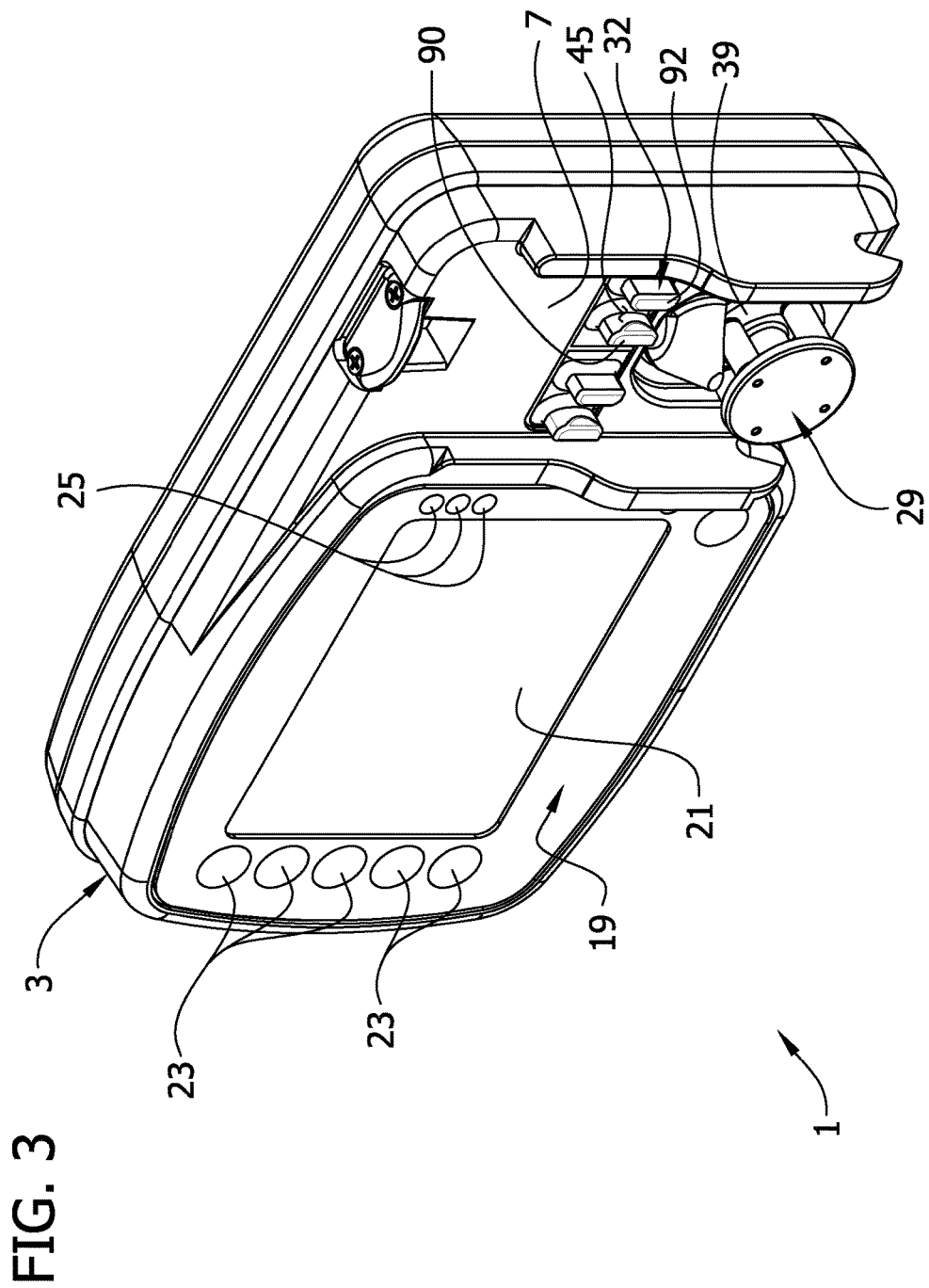
FIG. 3 is the perspective of FIG. 1 with the feeding set removed.

Referring to FIGS. 1 and 2, the flow control apparatus 1 may comprise a housing 3 adapted for loading the feeding set 5 (broadly, "pump set") to the flow control apparatus 1. The housing 3 may comprise a recess 7 (FIG. 3) for receiving a cassette 9 of the feeding set 5 to load the feeding set on the pump. The tubing 11 provides a fluidic pathway between a bag 12 of nutritional liquid and a patient (FIG. 1). The bag 12 is shown schematically in FIG. 1. The cassette 9 may mount the tubing 11 for engaging the tubing with the pump 1 when the cassette is received in the recess 7. The cassette 9 and feeding set 5 may be broadly considered a conduit assembly. Preferably, a means for driving fluid, such as a rotor 29, may be rotated by a motor 27 and adapted to engage the tubing 11.

As used herein, the portion of tubing 11 of the feeding set 5 leading to rotor 29 is termed "upstream," while the portion of tubing 11 leading away from rotor 29 is termed "downstream." Accordingly, rotation of rotor 29 compresses the tubing 11 and provides a means for driving fluid from the upstream to the downstream side of the feeding set 5 for delivery to a patient. As will be explained below, rotation of the rotor 29 to compress the tubing 11 also generates positive pressure within the tubing when an occlusion is present in the tubing. In the illustrated embodiment, the motor 27 and rotor 29 may broadly be considered "a pumping device." It is contemplated that any flow control apparatus having a means for driving fluid may be used, such as a linear peristaltic pump, bellows pump, turbine pump, rotary peristaltic pump, and displacement pump. Thus, various aspects of the invention can be implemented in other pumping devices. In addition, the illustrated embodiment discloses the valve mechanism 28 as a means for preventing fluid flow in the feeding set 5; however, any means that can prevent fluid flow through the feeding set may be used. Although an exemplary feeding set 5 is shown, feeding sets of other configurations and other types of pump sets (not shown) can be used.

Figure 4:
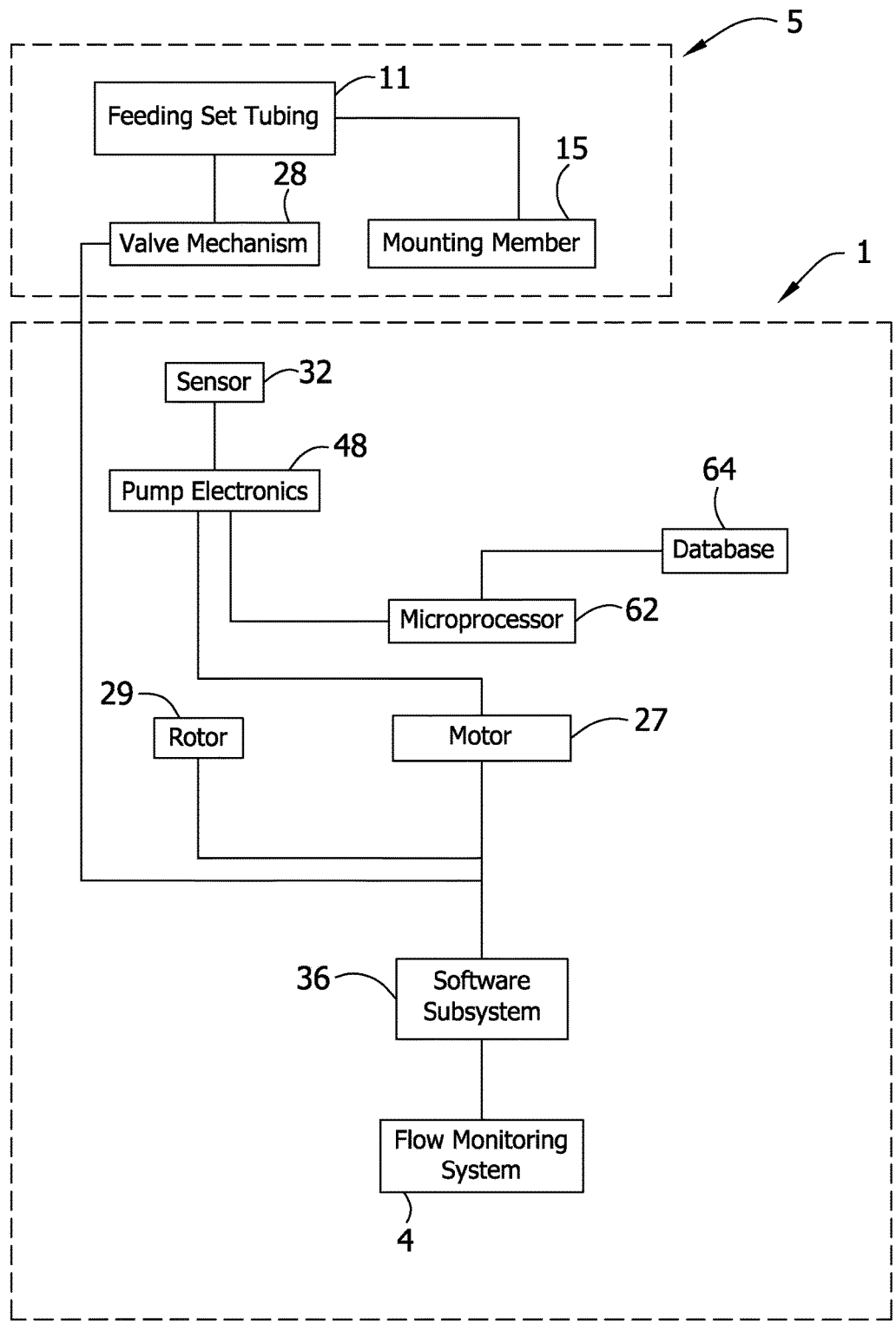
FIG. 4 is a block diagram illustrating the elements of the flow control apparatus including the flow monitoring system.

Referring to FIG. 4, the flow control apparatus 1 may further comprise a microprocessor 62 in operative association with one or more sensors 32 that detects or identifies at least one flow characteristic. A software subsystem 36 may be operatively associated with the microprocessor 62 and operatively associated with the flow monitoring system 4 to provide a means for the flow control apparatus 1 to detect and identify at least one flow characteristic, such as a downstream flow condition present in the feeding set 5. For example, the sensor 32 may comprise an ultrasonic sensor for detecting a change in pressure in the downstream side of the feeding set 5. The sensor 32 may be located on the housing 3 of the flow control apparatus 1 and positioned to detect pressure change in the downstream side of the feeding set 5. In the illustrated embodiment, the sensor 32 is positioned in the recess 7 and is adapted to securely receive the tubing 11 therein when the feeding set 5 is loaded on the flow control apparatus 1.

Referring to FIG. 1, the flow control apparatus 1 may further comprise a user interface 19 for interaction with the flow control apparatus 1. A display 21, in operative association with a plurality of buttons 23 may assist the user along with the microprocessor 62 to operate the flow monitoring system 4. The flow control apparatus 1 can further comprise light emitting diodes 25 on the housing 3.

In order for the sensor 32 to detect the change in pressure in the tubing 11 of the feeding set 5, the tubing may be engaged and retained within a sensor track 45 configured to receive the downstream side of the feeding set. Once the tubing 11 is engaged within the sensor track 45 and the remaining portions of the feeding set 5 are engaged to the apparatus 1, the flow monitoring system 16 may become operational. In some particular configurations, the detection and identification may be effected by measuring differences in time for ultrasonic pulses to propagate in the fluid flow direction, e.g., relative to a baseline propagation time.

Figure 12:
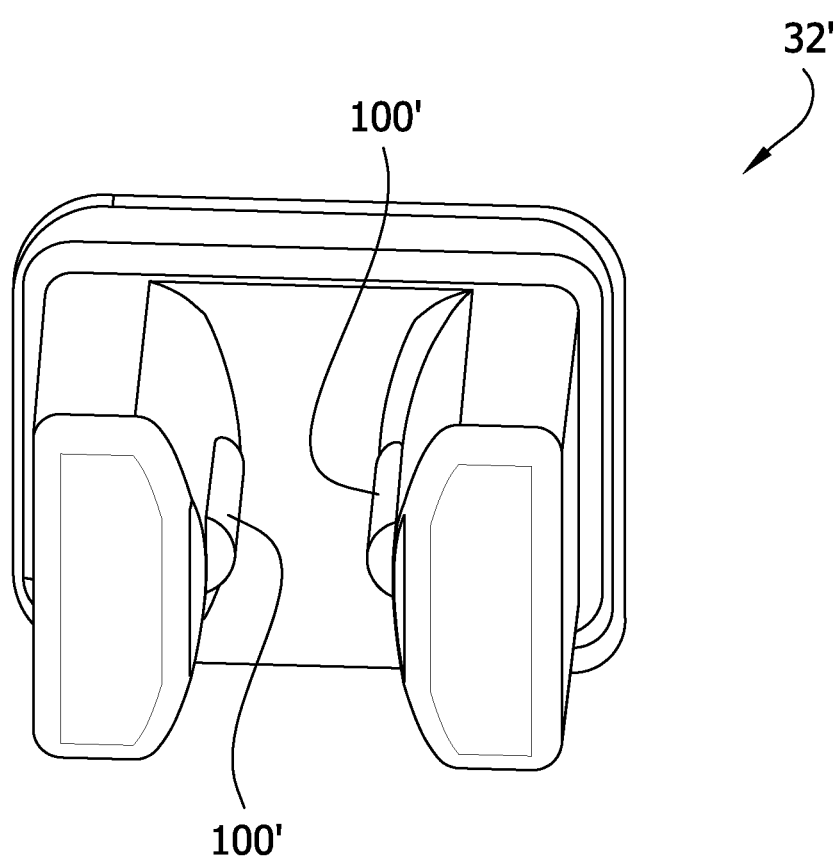
FIG. 12 is an enlarged perspective of a sensor of an enteral feeding pump.

Microprocessor 62 may control and manage the operation of the various components of the flow control apparatus 1. Preferably, the sensor 32 may comprise an ultrasonic transmitter assembly 90 that transmits an ultrasonic signal through the downstream portion of the tubing 11 seated in the sensor track 45 to detect pressure changes in the downstream side of the feeding set 5 when the signal is received by a receiver assembly 92. Upon receipt of the ultrasonic signal, receiver assembly 92 may detect the pressure within the tubing 11 along sensor track 42 based on the characteristics of the ultrasonic signal received by the microprocessor 62. The ultrasonic signal may detect the presence or absence of fluid in the tubing to give a basic indication of the operational status of the flow control apparatus 1. The ultrasonic signal may be responsive to the pressure in the tubing 11 such that an increase in pressure in the tubing will produce an increase in an amplitude of the signal. In particular, the compressing the tubing 11 by the rotor 29 when an occlusion in the tubing is present may cause the tubing to swell and increase a coupling of the tubing to the sensor 32. Therefore, the strength of the signal will increase with increased pressure on the downstream side of the feeding set 5. Conversely, a decrease in pressure in the tubing 11 may cause a decrease in the amplitude of the ultrasonic signal. The receiver assembly 92 may then communicate with the microprocessor 62. Based on the characteristics of the received ultrasonic signal communicated to the microprocessor 62, the software subsystem 36 may determine whether fluid flow within the feeding set 5 is normal or if a flow abnormality exists. A sensor 32' may include opposing ribs 100' on inner surfaces of the sensor (FIG. 12). The ribs 100' slightly reduce surface contact between the tubing 11 and the sensor 32 reducing the amplitude of the ultrasonic signal.

Software subsystem 36 may determine through a series of decision points and steps whether normal flow or abnormal flow conditions exist within tubing 11, and if an abnormal flow condition does exist, whether it is a downstream occlusion or a downstream air bubble in the tubing. A normal flow condition exists when a flow condition is not present that would occlude or obstruct fluid flow in the downstream side of the feeding set 5. In one embodiment, a pressure of between about 3 and about 5 psi is produced in the tubing 11 during non-occluded operation of the pumping device.

The microprocessor 62 may record readings from the sensor 32 in a database 64 (broadly, "memory"). In particular, a predetermined number of sensor signal readings may be stored in the database 64 in order from oldest signal to newest signal. Upon receiving a new signal reading, the database 64 may store the new signal reading as the newest signal reading. Once the predetermined number of signal readings is stored in the database 64, a new signal reading will discard the oldest signal reading, and the new signal reading will be stored as the newest signal reading in the database. The stored readings in the database 64 may be used by the microprocessor 62 to calculate a baseline pressure signal ("baseline"). The baseline can be updated as new readings from the sensor 32 are added to the database 64. The microprocessor 62 may use the baseline for occlusion and other flow condition determinations as will be described in more detail. It is to be understood that in the described embodiment, the flow monitoring system 4, the software subsystem 36, pump electronics 48, the microprocessor 62 and database 64 may be broadly considered "a control circuit." These components may be individually considered "a control circuit." Moreover, other types of control circuits may be used within the scope of the present invention.

Figure 6A:
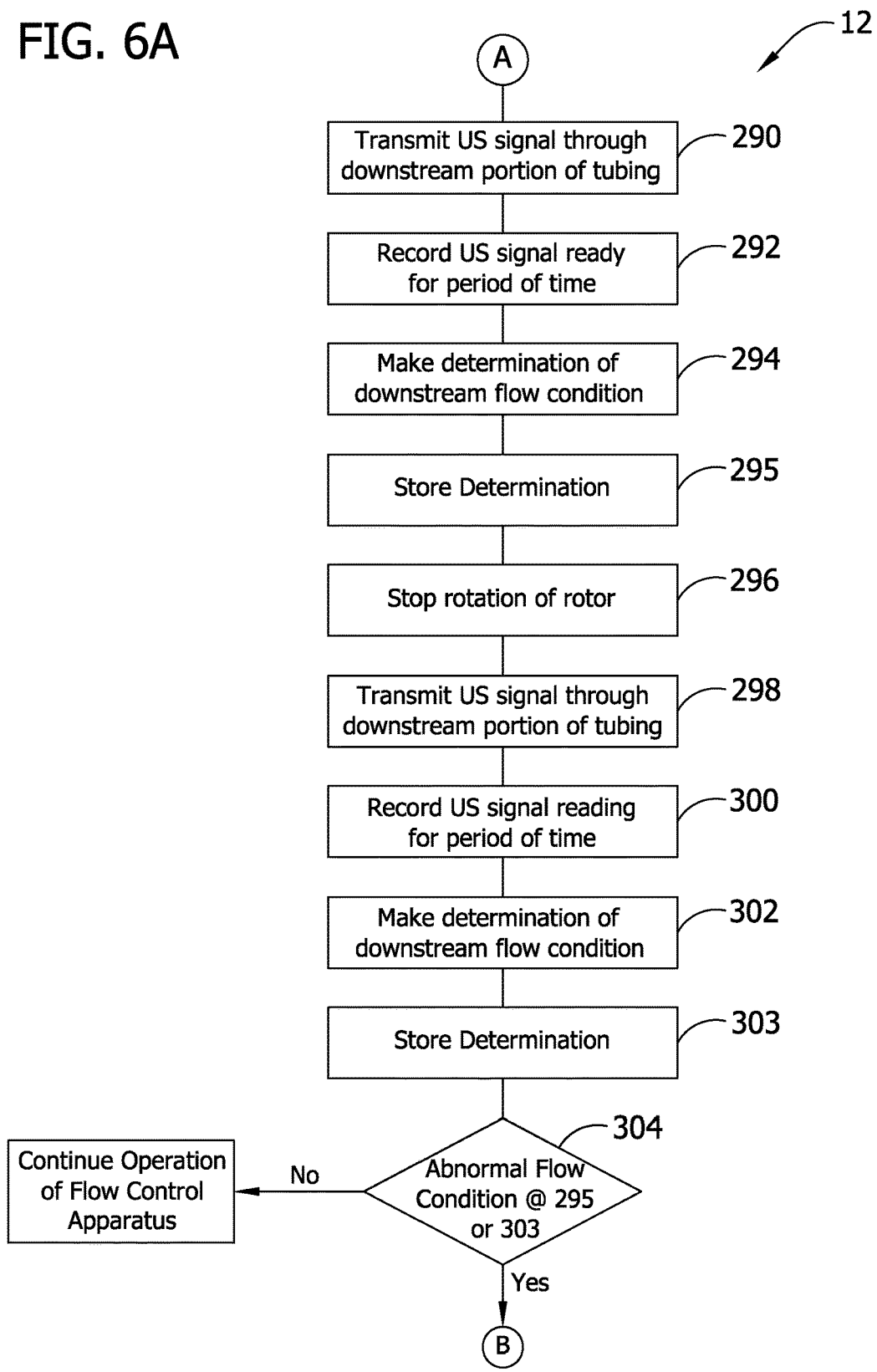
FIG. 6A is a first sub-routine of the flow chart in FIG. 5.
Figure 6B:
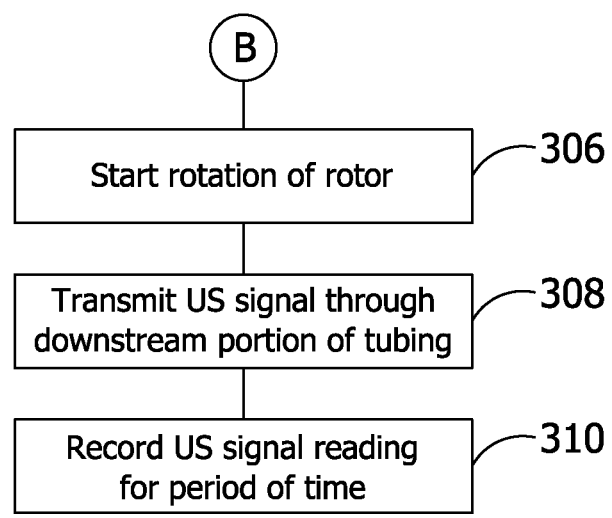
FIG. 6B is a second sub-routine of the flow chart in FIG. 5.
Figure 6C:
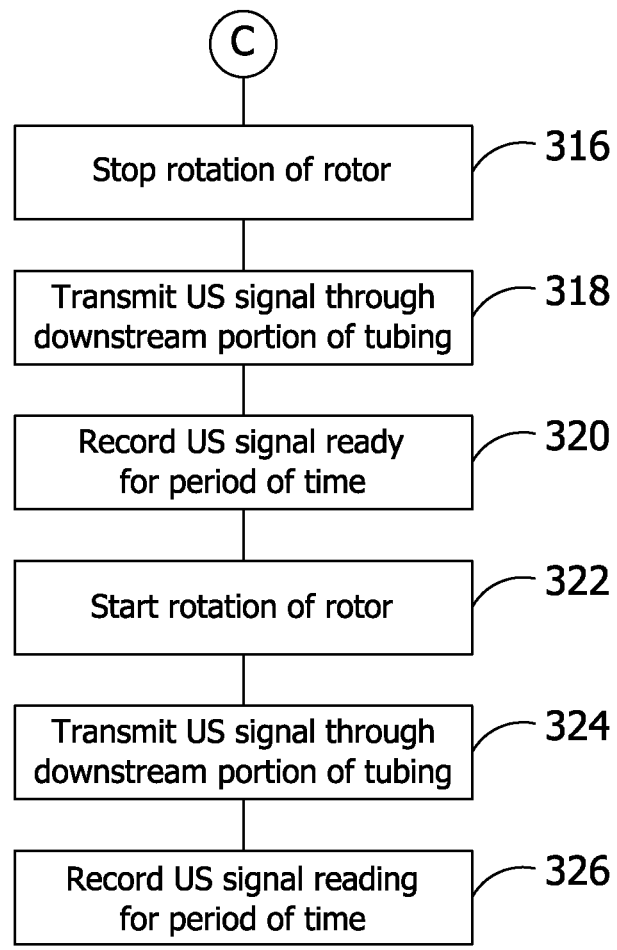
FIG. 6C is a third sub-routine of the flow chart in FIG. 5.
Figure 10:
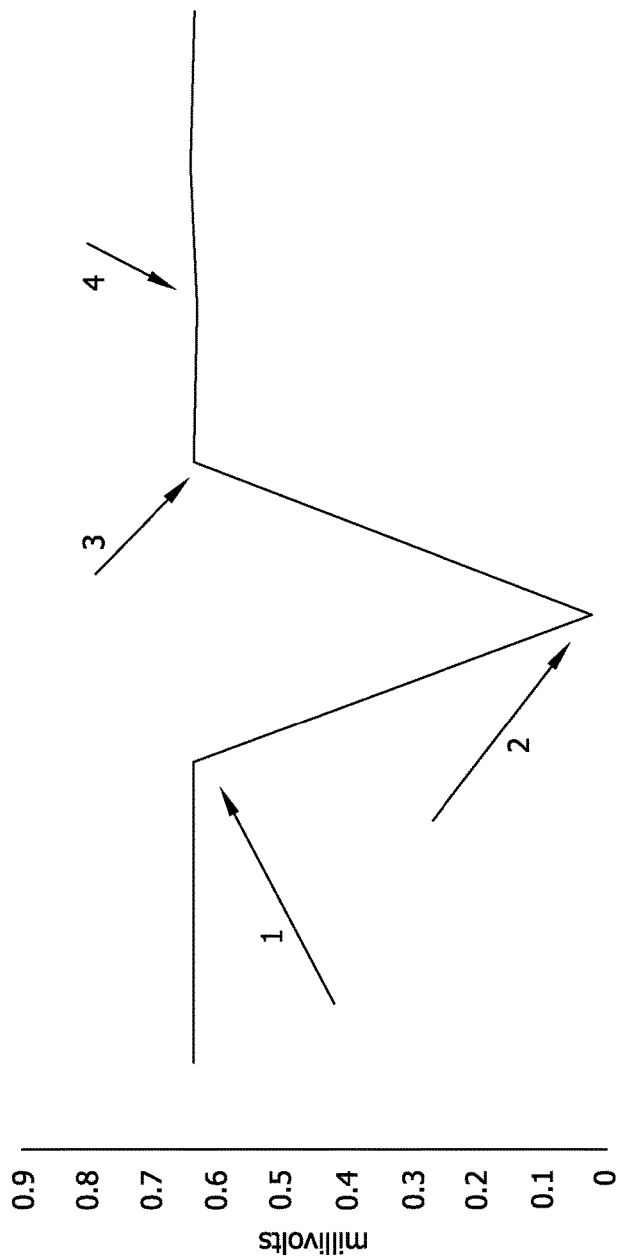
FIG. 10 is graph illustrating signal strength over time of an air bubble condition detected by the sensor of the flow monitoring system.
Figure 11:
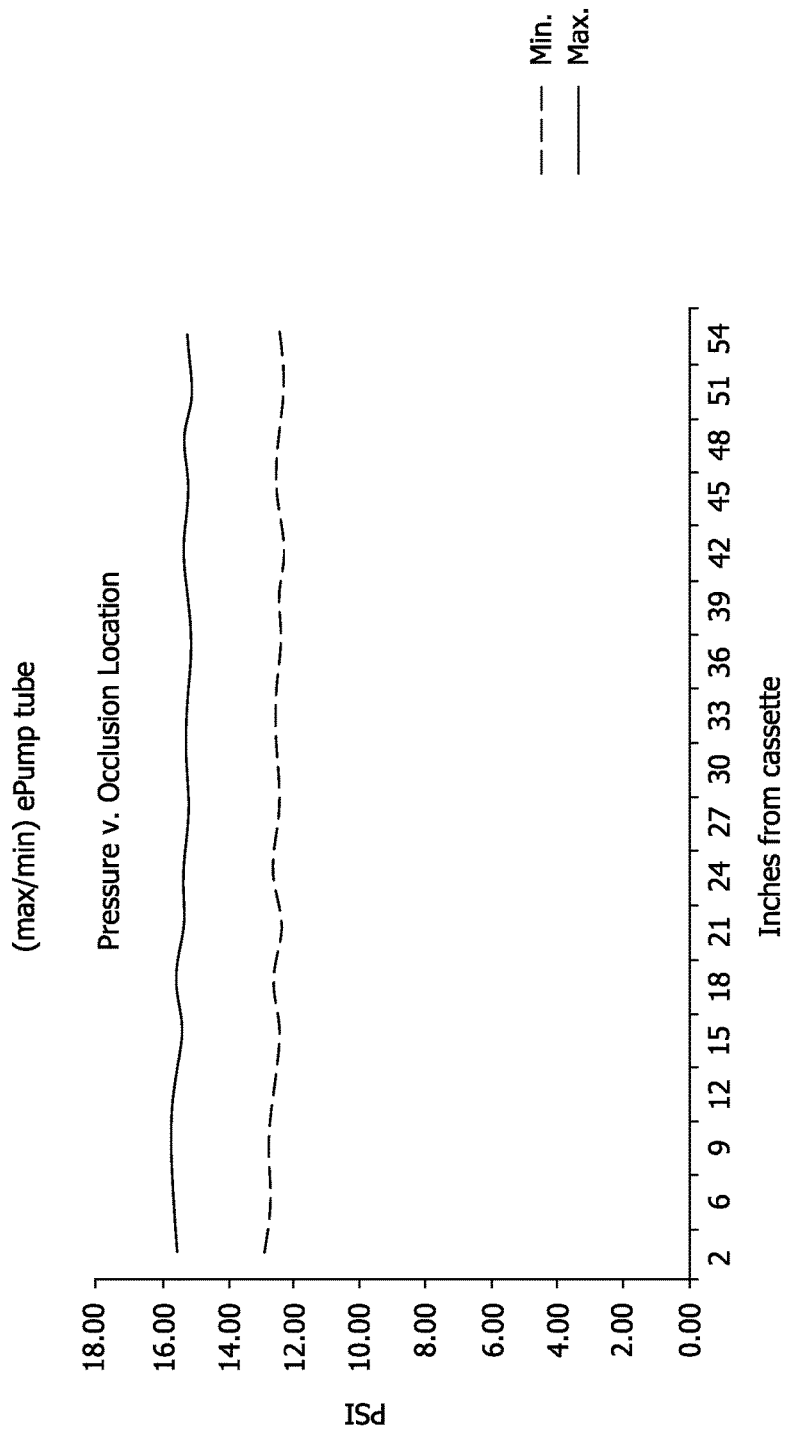
FIG. 11 is a graph illustrating pressure over a length of the feeding set when the feeding set is occluded.

Referring to the flow charts in FIGS. 5-6C, the various decision points and steps executed by software subsystem 36 to perform test procedures A-C by flow monitoring system 4 are illustrated. Software subsystem 36 may direct flow control apparatus 1 to perform various operations related to detecting a downstream flow conditions present in the feeding set 5. The graphs illustrated in FIG. 7-10 provide examples of predetermined signal profiles that represent the relative signal strengths of the ultrasonic signal received by the receiver assembly 92 for a non-occluded condition (FIG. 7), a typical running occlusion condition (FIG. 8), a slow running occlusion condition (FIG. 9), and an air bubble condition (FIG. 10). These will be used to aid in explaining the operation of the control circuit show in FIGS. 5-6C to determine whether occlusions or air bubbles exist in tubing 11. FIG. 11 illustrates a typical pressure in an occluded feeding set along the length the feeding set. In the embodiment of FIG. 11, the pressure generally ranges from about 12 psi to about 15 psi when an occlusion is present in the feeding set. It should be noted that while the graphs in FIGS. 7-10 depict examples of signal profiles, other profiles are envisioned for determining the various downstream flow conditions.

Figure 7:
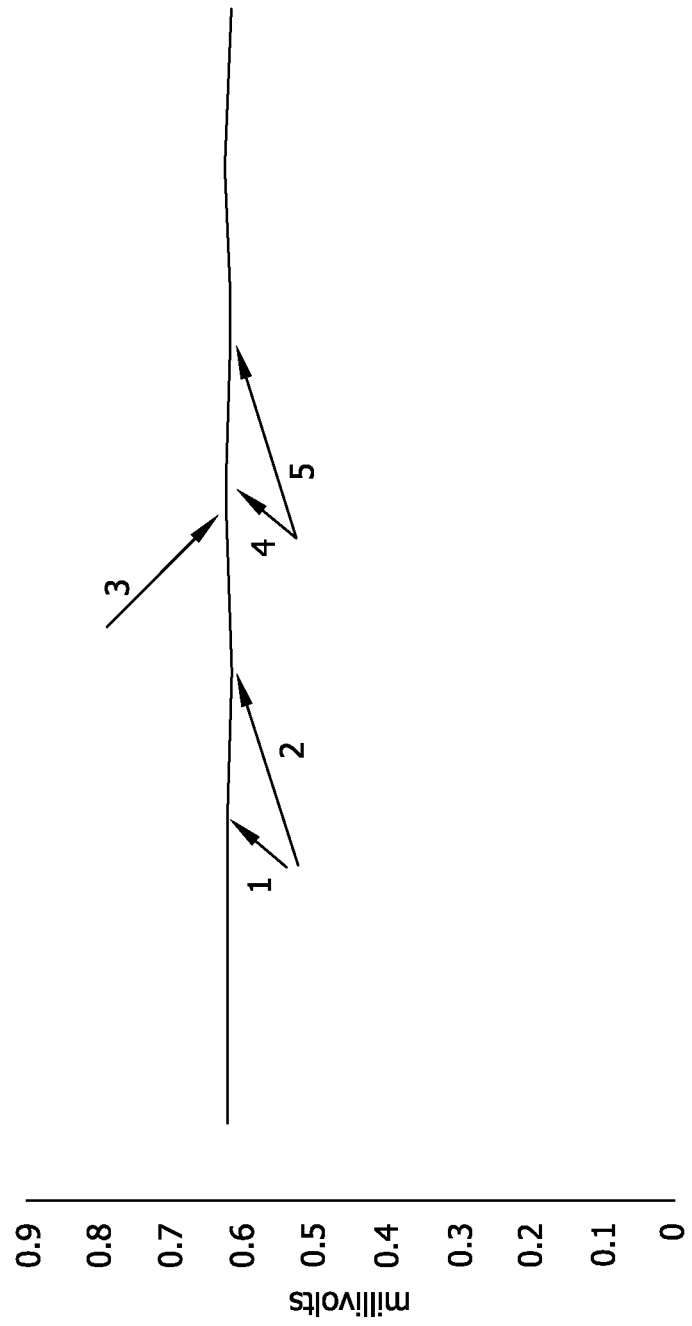
FIG. 7 is a graph illustrating signal strength over time for a non-occluded condition detected by a sensor of the flow monitoring system.
Figure 8:
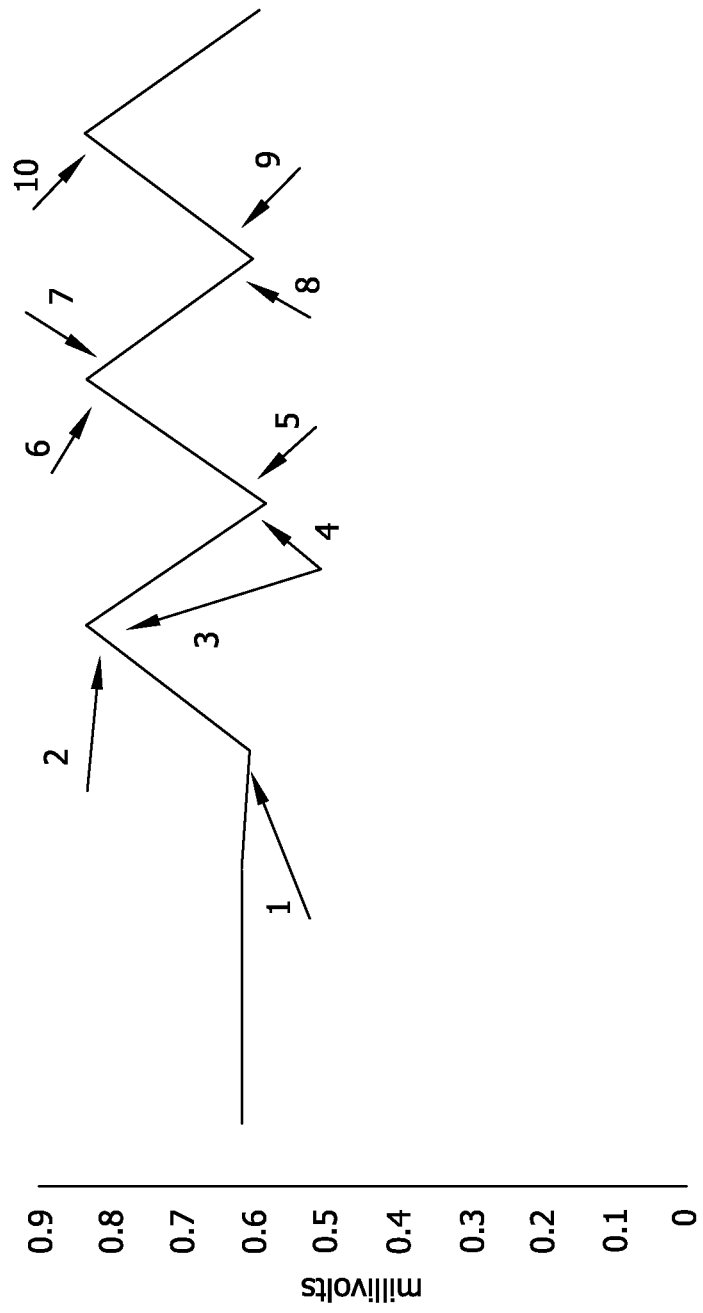
FIG. 8 is a graph illustrating signal strength over time for an occluded condition detected by the sensor of the flow monitoring system.
Figure 9:
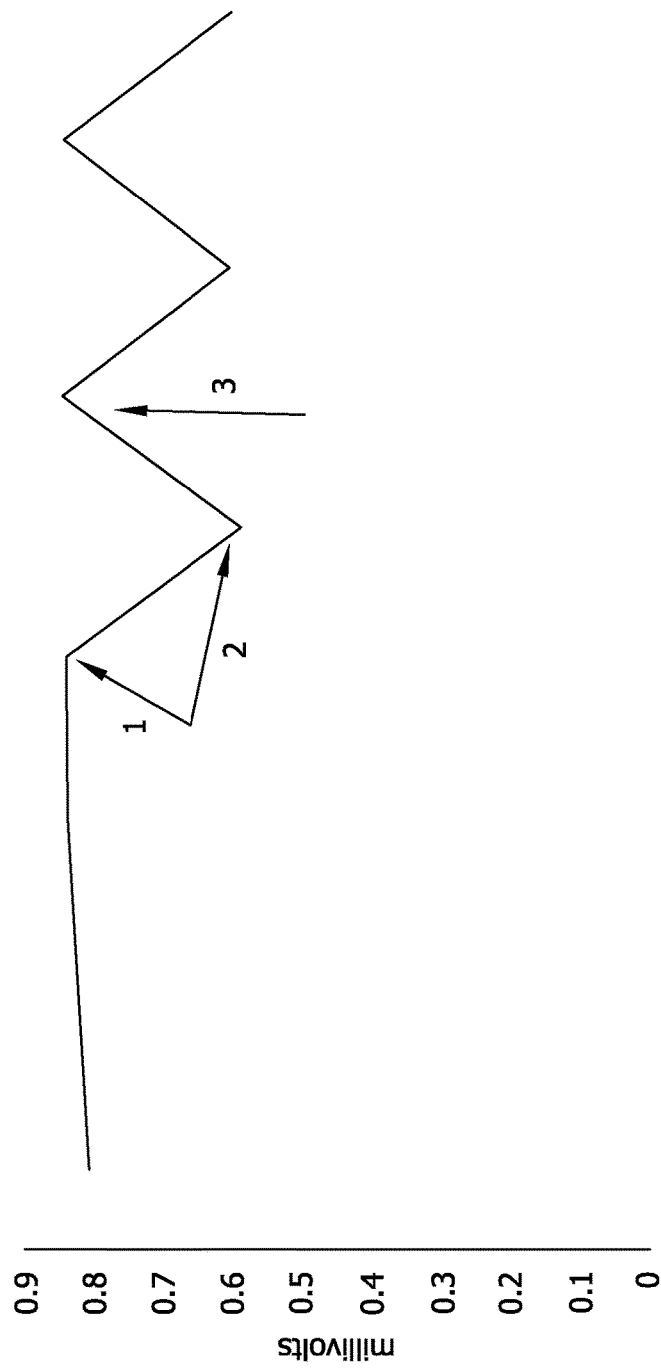
FIG. 9 is a graph illustrating signal strength over time for another occluded condition detected by the sensor of the flow monitoring system.

Referring to FIGS. 5 and 6A, at 287 the software subsystem 36 may determine whether the flow control apparatus 1 is operating such that the rotor 29 is rotating to deliver fluid through the feeding set 5. If so, at 290 the microprocessor 62 may instruct the sensor 32 to transmit ultrasonic signals through the downstream portion of the tubing 11 to provide the microprocessor with readings of the signals. At 292, the microprocessor may record the signal reading for a period of time. If during the reading an amplitude of the signal increases above a threshold level, the software subsystem 36 may determine at 294 that a downstream occlusion is present in the tubing 11. The software subsystem 36 may then store the determination of an occlusion in the database 64 at 295. This flow condition is illustrated at arrows 1 and 2 in FIG. 8. In one embodiment, the threshold level is a predetermined amount above the baseline. However, if the amplitude of the signal remains substantially constant during the reading (i.e., a steady reading), the software subsystem 36 may determine at 294 that a normal flow condition exists. If this is the case, the normal flow condition may be stored at 295. This flow condition is illustrated in FIG. 7. Even when the pump is activated and deactivated at points indicated by arrows in FIG. 7, only very small pressure changes are detected by the sensor 32. This is representative of an operation where no occlusions are present.

At step 296 the microprocessor 62 may instruct the flow control apparatus 1 to stop rotation of the rotor 29 at a "pressure release position." The pressure release position is a position of the rotor 29 that allows pressure in the tubing 11 to be released from the tube. At 298 the microprocessor 62 may instruct the sensor 32 to transmit an ultrasonic signal through the downstream portion of the tubing 11 to provide the microprocessor with a reading of the signal. At 300, the microprocessor may record the signal reading for a period of time. If during the reading the amplitude of the signal decreases from a level above the threshold level generally to the baseline, the software subsystem 36 may determine at 302 that a downstream occlusion is present in the tubing 11. The software subsystem 36 may then store the determination of an occlusion in the database 64 at 303. This flow condition is illustrated at arrows 3 and 4 in FIG. 8, arrows 1 and 2 in FIG. 9, and arrows 1 and 2 in FIG. 10. If the amplitude of the signal remains substantially constant during the reading, the software subsystem 36 may determine at 302 that a normal flow condition exists. If this is the case, the normal flow condition may be stored at 303. This flow condition is illustrated at arrows 1 and 2 in FIG. 7. At 304, if a normal flow condition determination was stored at 295 and 303, the software subsystem 36 may instruct the flow control apparatus 1 to continue operation. However, if an occlusion determination was stored at either 295 or 303, the software subsystem 36 may proceed to procedure B for verification.

Referring to FIGS. 5 and 6B, at step 306, the microprocessor 62 may instruct the flow control apparatus 1 to restart rotation of the rotor 29. The rotation may comprise a full or partial rotation of the rotor 29. At 308 the microprocessor 62 may instruct the sensor 32 to transmit an ultrasonic signal through the downstream portion of the tubing 11 to provide the microprocessor with a reading of the signal. At 310, the microprocessor may record the signal reading for a period of time. If during the reading the amplitude of the signal increases above the threshold level over the baseline, the software subsystem 36 may determine at 312 that a downstream occlusion is present in the tubing 11. This flow condition is illustrated at arrows 5 and 6 in FIG. 8. If during the reading at 308 the amplitude of the signal increases from below the baseline generally to the baseline, the software subsystem 36 may also determine at 312 that an occlusion is present in the downstream side of the feeding set 5. This flow condition is illustrated at arrows 2 and 3 in FIG. 9, and arrows 2 and 3 in FIG. 10. If during the reading at 310 the amplitude of the signal remains substantially constant, the software subsystem 36 may determine at 312 that a normal flow condition exists and continue operation of the flow control apparatus 1. This flow condition is illustrated at arrow 3 in FIG. 7.

In the instance where an occlusion determination was stored at either step 295 or step 303, the further determination of an occlusion at step 312 may be determined to be a verification of the previously determined occlusion. Thus, steps 306-312 may be broadly considered a verification routine. If an occlusion determination was stored at both 295 and 303, the further determination of an occlusion at step 312 may prompt the software subsystem 36 at 314 to declare that a downstream occlusion is present in the feeding set. The microprocessor 62 may sound an alarm 68 or stop operation of the apparatus 1 to repair or replace the feeding set 5 if the occlusion condition is declared at 314. If an occlusion determination was stored only at 303, the software subsystem may proceed to procedure C to test for a possible air bubble in the tubing 11.

Referring to FIGS. 5 and 6C, at step 316, the microprocessor 62 may instruct the flow control apparatus 1 to stop rotation of the rotor 29 at a pressure release position. At 318 the microprocessor 62 may instruct the sensor 32 to transmit an ultrasonic signal through the downstream portion of the tubing 11 to provide the microprocessor with a reading of the signal. At 320, the microprocessor may record the signal reading for a period of time. At 322 the microprocessor 62 may instruct the flow control apparatus 1 to restart rotation of the rotor 29. The rotation may comprise a full or partial rotation of the rotor 29. At 324 the microprocessor 62 may instruct the sensor 32 to transmit an ultrasonic signal through the downstream portion of the tubing 11 to provide the microprocessor with a reading of the signal during and after rotation of the rotor 29. At 326, the microprocessor may record the signal reading for a period of time. If during the reading at 320 the amplitude of the signal decreases from a level above the threshold level generally to the baseline, and if during the reading at 326 the amplitude of the signal increases above the threshold level over the baseline, the software subsystem 36 may declare at 328 that a downstream occlusion is present in the tubing 11. This flow condition is illustrated at arrows 7-10 in FIG. 8. The microprocessor 62 may sound an alarm 68 or stop operation of the apparatus 1 to repair or replace the feeding set 5. If during the reading at 320 and 326 the amplitude of the signal remains substantially constant, the software subsystem 36 may declare at 328 that an air bubble is present in the downstream side of the feeding set 5. This flow condition is illustrated at arrow 4 in FIG. 10. The microprocessor 62 may sound an alarm 68 or stop operation of the apparatus 1 to repair or replace the feeding set 5.

Preferably, alarm 68 may be audible, visual, vibratory or any combination thereof. In one embodiment, a certain type of alarm 68 may represent a specific abnormal flow condition detected within the feeding set 5 and identifiable to the user by its own unique visual, audible and/or vibratory alarm 68. In one embodiment, the alarm 68 may cause a particular message to appear on the display 21. In addition or as an alternative, the alarm 68 may have different sounds could indicate different types of downstream flow conditions, such as a downstream occlusion or a downstream air bubble. These unique alarms 68 allow for flow monitoring system 4 to signal the presence of several different abnormal flow conditions.

Although the flow control apparatus 1 described above is an exemplary embodiment, the flow monitoring system 4 can be used with any suitable flow control apparatus.

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the microprocessor 62 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A flow control apparatus adapted to load a feeding set having an upstream side and a downstream side, said flow control apparatus comprising:
    a housing capable of receiving at least a portion of the feeding set;
    a pumping device contacting the feeding set when the feeding set is received by the housing so the pumping device acts on the feeding set to produce fluid flow in the feeding set for delivery of fluid to a subject, wherein the pumping device comprises a motor and a rotor, the motor being adapted to rotate the rotor so that the rotor repeatedly contacts the feeding set to produce fluid flow through the feeding set;
    an ultrasonic sensor arranged with respect to the pumping device to detect a change in pressure in the downstream side of the feeding set when the feeding set is loaded on the apparatus; and
    a control circuit in communication with the ultrasonic sensor for receiving a sensor signal from the ultrasonic sensor indicative of the pressure in the downstream side of the feeding set, the control circuit being configured to make a first determination of a downstream flow condition of the feeding set while fluid is flowing through the feeding set, to make a second determination of the downstream flow condition, and if at least one of the first and second determinations of the downstream flow conditions indicates an occlusion the control circuit is adapted to operate the pumping device in a verification routine to make a third determination of the downstream flow condition, and if the third determination indicates an occlusion, but only a one of the first and second determinations indicated an occlusion to make a fourth determination of the downstream flow condition.

2. The flow control apparatus set forth in claim 1 wherein the ultrasonic sensor comprises a receiver assembly and an ultrasonic transmitter assembly, the transmitter assembly being configured to transmit the ultrasonic signals through the downstream side of the feeding set to the receiver assembly for determining the downstream flow condition of the feeding set when the feeding set is loaded on the apparatus.

3. The flow control apparatus set forth in claim 1 wherein the control circuit includes a memory, the control circuit being configured to save a series of sensor signal readings in the memory, the control circuit being configured to use the saved sensor signal readings to establish a baseline.

4. The flow control apparatus set forth in claim 3 wherein the control circuit is configured to store a predetermined number of sensor signal readings in the memory including an oldest sensor signal reading and a newest sensor signal reading, and upon receiving a next sensor signal reading making a total number of sensor signal readings higher than said predetermined number, to discard the oldest sensor signal reading and store said next sensor signal reading as the newest sensor signal reading.

5. The flow control apparatus set forth in claim 3 wherein the control circuit, for making the first determination of the downstream flow condition, is configured upon receiving a new sensor signal reading to determine that the new sensor signal reading is above the baseline.

6. The flow control apparatus set forth in claim 3 wherein the control circuit, for making the second determination, is configured to cease rotation of the rotor at a predetermined position causing pressure in the feeding set to decrease, and to monitor the ultrasonic signal for a decrease to the baseline.

7. The flow control apparatus as set forth in claim 3 wherein the control circuit, for making the second determination of the downstream flow condition, is configured upon receiving a new sensor signal reading when the pumping device is not operating to produce fluid flow to determine that the new sensor signal readings are falling to the baseline.

8. The flow control apparatus as set forth in claim 7 wherein the control circuit, for making the second determination of the downstream flow condition, is configured to stop the pumping device at a predetermined position before receiving said new sensor signal readings.

9. The flow control apparatus set forth in claim 8 wherein the predetermined position comprises a rotational position of the rotor where fluid pressure in the feeding set is released.

10. The flow control apparatus set forth in claim 8 wherein the control circuit, for making the third determination of the downstream flow condition, is configured to cause further rotation of the rotor, the pressure in the feeding set increasing upon said further rotation when an occlusion is present, and to monitor the ultrasonic signal for an increase in pressure above the baseline in response to the increase in pressure caused by said further rotation of the rotor.

11. The flow control apparatus of claim 3 wherein the baseline established by the control circuit is a pressure reading indicative of normal flow conditions in the flow control apparatus in which no occlusion is present.

12. The flow control apparatus of claim 11 wherein the baseline is between 3 psi and 5 psi.

13. The flow control apparatus as set forth in claim 3 wherein the memory stores a threshold comprising a pressure above the baseline.

14. The flow control apparatus as set forth in claim 13 wherein the control circuit monitors sensor signals from the ultrasonic sensor for an increase in amplitude above the threshold for making the first determination of the downstream flow condition.

15. A method of operating a flow control apparatus including a pumping device for detecting occlusions in fluid flow in a pump set acted upon by the flow control apparatus in a downstream portion of the pump set located downstream of the pumping device, wherein the pumping device comprises a motor and a rotor, the motor being adapted to rotate the rotor so that the rotor repeatedly contacts the pump set to produce fluid flow through the pump set, the method comprising:
- receiving in a control circuit sensor signals from an ultrasonic sensor positioned to detect pressure in the downstream portion of the pump set;
- comparing the received sensor signals to a baseline stored in the control circuit;
- making with the control circuit a first determination of the presence of an occlusion in the downstream portion of the pump set using the comparison of the received sensor signals to the baseline;
- making a second determination of the downstream flow condition,
- and if at least one of the first and second determinations of the downstream flow conditions indicates an occlusion, operating a verification routine to make a third determination of the downstream flow condition
- and if the third determination indicates an occlusion, but only a one of the first and second determinations indicated an occlusion to make a fourth determination of the downstream flow condition.

16. The method set forth in claim 15 wherein the step of comparing comprises determining if the received sensor signals are above the baseline when the pumping device is activated to pump fluid through the pump set for making the first determination of the downstream flow condition.

17. The method as set forth in claim 15 wherein the step of comparing comprises determining if the received sensor signals are falling to the baseline for making the second determination of the downstream flow condition.

18. The method as set forth in claim 15 further comprising storing sensor signals readings from the ultrasonic sensor and using the stored sensor signals to establish the baseline.

19. A flow control apparatus adapted to load a feeding set having an upstream side and a downstream side, said flow control apparatus comprising:
- a housing capable of receiving at least a portion of the feeding set;
- a pumping device contacting the feeding set when the feeding set is received by the housing so the pumping device acts on the feeding set to produce fluid flow in the feeding set for delivery of fluid to a subject, wherein the pumping device comprises a motor and a rotor, the motor being adapted to rotate the rotor so that the rotor repeatedly contacts the feeding set to produce fluid flow through the feeding set;
- a sensor arranged with respect to the pumping device to detect a change in pressure in the downstream side of the feeding set when the feeding set is loaded on the apparatus; and
- a control circuit in communication with the sensor for receiving a sensor signal from the sensor indicative of the pressure in the downstream side of the feeding set, the control circuit being configured to determine a downstream flow condition of the feeding set while fluid is flowing through the feeding set, wherein the control circuit is configured to stop the pumping device at a predetermined position during an occlusion detection procedure, wherein the predetermined position comprises a rotational position of the rotor where fluid pressure in the feeding set is released and an occlusion is determined when the received sensor signals decrease from a level above a threshold occlusion level to a baseline level when the pumping device is stopped at the predetermined position.

* * * * *